United States Patent [19]

Schwartz et al.

[11] Patent Number: 4,847,284

[45] Date of Patent: Jul. 11, 1989

[54] ANTIFUNGAL FERMENTATION PRODUCT AND DERIVATIVES AND COMPOSITIONS THEREOF

[75] Inventors: Robert E. Schwartz, Westfield; Janet C. Onishi, Mountainside; Richard L. Monaghan, Somerset; Jerrold M. Liesch, Princeton Junction; Otto D. Hensens, Red Bank, all of N.J.

[73] Assignee: Merck & Co., Inc., Rahway, N.J.

[21] Appl. No.: 172,164

[22] Filed: Mar. 23, 1988

[51] Int. Cl.[4] .................. C07D 207/24; A61K 31/40
[52] U.S. Cl. .................... 514/424; 548/541; 435/121
[58] Field of Search .................. 548/541; 514/424

[56] References Cited

FOREIGN PATENT DOCUMENTS 0257966 11/1986 Japan ..................... 548/45

OTHER PUBLICATIONS

A. Jimenez et al., "Antibiotics", vol. V, part 2, pp. 1–19, Springer-Verlag, Berlin-Heidelberg, New York (1979).
Sobin et al., JACS, 76, p. 4053 (1954).
Tanner et al., Antibiot. Annual, 1954–1955, p. 809.

*Primary Examiner*—David B. Springer
*Attorney, Agent, or Firm*—Alice O. Robertson; Michael C. Sudol

[57] ABSTRACT

A novel pyrrolidinol isolated from the fermentation of *Aspergillus ochraceus* and certain derivatives thereof are described. The compounds are broad spectrum antifungal agents.

5 Claims, No Drawings

ANTIFUNGAL FERMENTATION PRODUCT AND DERIVATIVES AND COMPOSITIONS THEREOF

The present invention is concerned with an antifungal pyrrolidine antibiotic agent produced by fermentation of Aspergillus ochraceus and derivatives thereof and to compositions containing these agents.

BACKGROUND OF THE INVENTION

Various metabolites have been reported as having been produced from various isolates of Asperigillus ochraceus. Turner, W.B. et al, "Fungal Metabolites II" pp 87, 90, 128, 164, 198, 316, 416, Academic Press, London, 1983. These include ochratoxin, xanthomegnin, mellein, viomellein, trypacidin, aspyrone, ergosta-4,6,8(14),22-tetraene-3-one, flavacol, penicillic acid and modified asperigillic acids. None of these are pyrrolidine compounds.

A pyrrolidine antibiotic has been reported. It is, an antiprotozoan and anti-yeast compound, isolated from *Streptomyces griseolus* and *Streptomyces roseochromogenes*. B.A. Sobin et al., J. Am. Chem. Soc. 76, 4053 (1954); F.W. Tanner et al., Antibio. Ann. 1954–55, 809; A. Jimenez et al., "Anisomycin and Related Antibiotics" in "Antibiotics", Vol. V, Part 2 "Mechanism of Action of Antieukaryotic and Antiviral Compounds," F.F. Hahn, Ed., pp 1–19, Springer-Verlag, Berlin, New York 1979.

DESCRIPTION OF THE INVENTION

It has now been discovered that a wholly different antibiotic fermentation product which has broad antifungal properties may be obtained by the controlled cultivation of the microorganism, *Aspergillus ochraceus*. The antibiotic fermentation product is believed to be a pyrrolidinol compound and the present invention is directed to said fermentation product and acylated derivatives thereof which may be represented by the formula

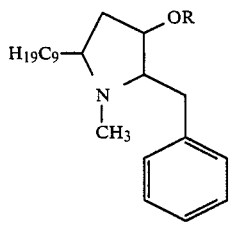

(I)

wherein R is H or lower alkanoyl; and to a process for preferentially producing the desired antibiotic.

The formula of the novel antibiotic fermentation product is based on spectral data and other physical data together with the spectral data of the acetyl derivative as hereinafter detailed. The compound may be identified by the name 2-benzyl-1-methyl-5-(n-nonyl)-pyrrolidin-3-ol. For convenience, the compound in which R=H, hereinafter shall be referred to as Compound IA.

The novel antibiotic agent, Compound IA, is a white, waxy or light colored solid which may be characterized by the following physical properties:

Mass spectral data

The molecular formula of this compound is $C_{21}H_{35}NO$ (317 amu) as disclosed by its electron impact mass spectrum which exhibits significant ions at m/z 316.2635 (M-H; calc for $C_{21}H_{34}NO$ 316.2640), 298 (316-$H_2O$), 226.2165 (M-$C_7H_7$; calc for $C_{14}H_{28}NO$ 226.2171), and 190.1224 (M-$C_9H_{19}$; calc for $C_{12}H_{16}NO$ 190.1232). The fast atom bombardment spectrum contains a pseudo-molecular ion at m/z 318 corresponding to $(M+H)^+$.

A mono-trimethylsilyl (TMS) derivative is formed by treatment with bistrimethylsilyltrifluoroacetamide (BSTFA) and pyridine and the TMS spectrum contains the following significant ions: 388.3030 (M+$SiC_3H_8$-H; calc for $C_{21}H_{34}NO+SiC_3H_8$ 388.3036), 374.2860 (M+$SiC_3H_8$—$CH_3$; calc for $C_{21}H_{35}NO+SiC_2H_5$ 374.2879), 298.2561 (M+$SiC_3H_8$-$C_7H_7$: calc for $C_{14}H_{28}NO+SiC_3H_8$ 298.2566), and 262.1619 (M+$SiC_3H_8$—$C_9H_{19}$; calc for $C_{12}H_{16}NO+SiC_3H_8$ 262.1627).

The presence of a silyl group in the ions was confirmed by comparison with the perdeutero-TMS derivative formed with $d_{18}$-BSTFA and pyridine.

NMR data $^{13}C$ NMR ($CDCl_3$, 100 MHz in ppm downfield of tetramethylsilane TMS at room temperature). 14.1q, 22.7t, 26.3t, 29.3t, 29.58t, 29.65t, 29.9t, 31.9t, 33.6t, 34.8t, 38.6q, 39.3t, 66.0d, 70.4d, 73.7d, 126.1d, 128.4(2X)d, 129.4(2X)d, 139.4s.

$^1H$ NMR ($CD_3CO_2D$ at 400 MHz in ppm downfield of TMS using the solvent peak at $\beta$ 2.03 as reference) 3.14dd (1H,J=5,13.5), 3.29dd (1H,J=10, 13.5), 3.47dt (1H,J=10,~4.5), 4.33ddd (1H,J=1.5, 4.3, 6.8), 1.93 (1H,J=1.5, 7.2, 14.8), 2.65ddd (1H,J=6.8, 9.8, 14.8), ~3.31 (1H,obsc), ~2.03 (1H,m), ~1.76 (1H,m), ~1.28 (~14H,m), 0.88 t(3H,J-6.8).

(s-singlet; d=doublet; t=triplet; q=quartet; m=multiplet; obsc=oscured (overlapping signals)).

The acetyl derivative (R =$CH_3CO$) exhibited the following $^{13}C$ NMR characteristics: $^{13}C$ NMR ($CDCl_3$, 100 MHz in ppm downfield of TMS at R.T.) 14.1q, 21.3q, 22.7t, 26.5t, 29.3t, 29.5t, 29.6t, 29.7t, 31.8t, 33.9t, 34.6t, 37.9q, 39.3t, 66.2d, 71.7d, 73.3d, 126.2d, 128.4(2X)d, 128.9(2X)d, 138.9s, 170.7s.

The compounds of the present invention identified by formula I are white or light colored solids soluble in organic solvents and adaptable to be employed in solution. They are also adaptable to be employed in aqueous dispersions.

The nove pyrrolidinol antibiotic and the acyl derivatives thereof are broad spectrum antifungal agents active against both yeasts and filamentous fungi. They are not only suitable for topical treatment of yeast and fungal infections but in view of the broad spectrum exhibited, they are also adapted to be employed anywhere where control of fungi is desired. Thus, the compound may be employed to control not only the growth of fungi causing mycotic infections in human and animal species but also those which are allergens, are plant pathogens or which cause rot or other deterioration in products such as paints, textiles, wood, wood products, and paper products. The compounds are especially useful against plant-infecting fungi such as *Alternaria solani* and *Cochliobolus miyabeanus*. Some other specific filamentous fungi and yeasts against which the compounds are useful include *Verticillium serrae, Cercospora beticola, Cephalosporium* sp., *Cryptococcus laurentii, Cryptococcus albidus, Rhizomucor miehei, Aspergillus flavus, Aspergillus fumigatus, Ceratocystis ulmi*. The compounds are also active against certain bacteria such as Streptomyces species.

The antibiotic antifungal agent of the present invention, Compound IA, is conveniently produced by cultivating a strain of *A. ochraceus*, on deposit and obtainable from the culture collection of American Type Culture Collection, 12301 Parklawn Drive, Rockville, Md. 20852 and having the accession number ATCC 22947, and recovering said Compound IA from the culture medium.

Although the invention is discussed herein below principally with respect to the specific strain, it is well-known in the art that the properties of microorganisms may be varied naturally and artificially. Thus, all strains of *Aspergillus ochraceus* ATCC 22947, including variants and mutants, whether obtained by natural selection, produced by the action of mutating agents such as ionizing radiation or ultraviolet irradiation, or by the action of chemical mutagens such as nitrosoguanidine, are contemplated to be within the scope of this invention.

Compound IA of the present invention may be produced during aerobic fermentation of suitable nutrient media under conditions hereinafter described with a producing strain of *Aspergillus ochraceus* ATCC 22947, and thereafter recovering the active component from the fermentation medium.

The fermentation is carried out in a media containing sources of carbon and nitrogen assimilable by the microorganisms and generally low levels of inorganic salts. In addition, the media may be supplemented with trace metals, although if complex sources of carbon and nitrogen are employed, they are usually present in the complex sources.

The sources of carbon include glycerol, sugars, starches and other carbohydrates or carbohydrate derivatives such as dextrose, citrate as well as complex nutrients such as corn meal, pectin, corn, cod liver oil and the like. The exact quantity of the carbon source which is utilized in the medium will depend, in part, upon the other ingredients in the medium, but it is usually found that an amount of carbohydrate between 0.5 and 50 percent by weight of the medium is satisfactory. These carbon sources can be used individually or several such carbon sources may be combined in the same medium.

The sources of nitrogen include the amino acid glycine and ammonium sulfate as well as complex sources such as yeast hydrolysates, yeast autolysates, tomato paste, soybean meal, corn steep liquors, lard water, tomato paste and the like. The various sources of nitrogen can be used along or in combination in amounts ranging from 0.2 to 50 percent by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium, and the like.

In the preferred process for carrying out the fermentation for preferentially producing the desired antibiotic, Compound Ia, the fermentation medium designed is one rich in carbon sources. By "rich" is meant from about 50 to 70 percent by weight of the added solid nutrients.

The media suitable for carrying out the fermentation may be solid or liquid.

A good solid medium is one which has a corn base a representative medium is the following:

| Component | Weight or Volume Per 250 ml Flask | |
|---|---|---|
| Medium A | | |
| Cracked corn | 10.0 | grams |
| Yeast hydrolysate (Ardamine, PH) | 2.0 | mg |
| $KH_2PO_4$ | 1.0 | mg |
| $MgSO_4.7H_2O$ | 1.0 | mg |
| Sodium tartrate | 1.0 | mg |
| $FeSO_4.7H_2O$ | 0.1 | mg |
| $ZnSO_4.H_2O$ | 0.1 | mg |
| Distilled water | 25 | ml |

Representative liquid media are the following:

| Medium B | | |
|---|---|---|
| Dextrose | 10 | g |
| Glycerol | 10 | ml |
| Corn steep liquor | 5 | ml |
| $(NH_4)_2SO_4$ | 2 | g |
| Corn meal | 10 | g |
| $COCl_2.6H_2O$ | 10 | mg |
| Soybean meal | 5 | g |
| Glycine | 2 | g |
| Distilled water | to 1000 | ml |
| pH 7.0 | | |
| Medium C | | |
| Dextrose | 10 | g |
| $KH_2PO_4$ | 2 | g |
| Glycerol | 10 | ml |
| Corn meal | 10 | g |
| Lard water | 5 | g |
| $CoCl_2.6H_2O$ | 10 | mg |
| Pectin | 10 | g |
| Polyglycol P2000 | 2 | ml |
| Tomato paste | 5 | g |
| Distilled water | to 1000 | ml |
| pH 7.0 | | |
| Medium D | | |
| Glycerol | 10 | ml |
| $KH_2PO_4$ | 2 | g |
| $(NH_4)_2SO_4$ | 2 | g |
| Corn meal | 10 | g |
| Pectin | 10 | g |
| Soybean meal | 5 | g |
| Polyglycol P2000 | 2 | ml |
| Cod liver oil | 2 | ml |
| Sodium citrate | 2 | g |
| Distilled water | to 1000 | ml |
| pH 7.0 | | |

For producing Compound IA of the present invention, a fermentation medium containing ATCC 22947 is prepared by inoculating spores or mycelia of the antibiotic-producing organism into a suitable medium and then cultivating under aerobic conditions.

The procedure generally is first to inoculate a preserved source of culture from an agar slant containing nutrient medium into a nutrient seed-producing medium and to obtain, preferably through a two step procedure, growth of the organisms which serve as seeds in the production of the antifungal agent. A representative seed medium is that having the following composition:

| Seed Medium | | |
|---|---|---|
| Corn steep liquor | 5 | g |
| Tomato paste | 40 | g |
| Oat flour | 10 | g |

-continued

| Seed Medium | |
|---|---|
| Glucose | 10 g |
| Trace Elements Mix | 10 ml |
| Distilled water | to 1000 ml |
| pH 6.8 | |
| Trace Elements Mix: | |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Water | to 1000 ml |

In carrying out the process, a slant section of a preserved culture of Aspegillus ochraceus ATCC 22947 is inoculated into an appropriate liquid nutrient seed medium of pH in the range 5 to 8.1, optimally 6 to 7.5, and the flask incubated with or without agitation at temperatures in the range of from about 15° C. to about 30° C., preferably 20° to 28° C. Agitation when employed, may be up to 400 rpm, preferably, about 200 to 220 rpm. The incubation is carried out over a period of from 2 to 30 days, preferably 2 to 14 days. When growth is abundant, usually between 2 and 5 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 3 days. The growth from the second stage may then be employed to inoculate the production medium.

The fermentation production medium inoculated with the culture growth is incubated for 3 to 30 days, usually 7 to 14 days, preferably with but also without agitation. The fermentation may be conducted aerobically at temperatures ranging from about 20° C. to about 40° C. Airflow may be from 2.0 to 5.0 liters per minute and agitation may be at a rate of 200 to 500 rpm. For optimum results, it is most convenient to conduct these fermentations at a temperature in the range of from about 24° C. to about 30° C. Temperatures of about 24°-28° C. are most preferred. The pH of the nutrient medium suitable for producing the instant compounds can vary from about 5.0 to 8.5 with a preferred range of from about 6.0 to 7.5. After the appropriate period for the production of the desired compound, the latter is recovered from the fermentation medium as hereinafter more fully described.

The active material may be recovered by the steps comprising (1) adding alcohol to said medium, stirring, steeping and thereafter filtering to recover the active component in the resulting alcoholic solution;

(2) adding water to the alcoholic solution to convert it to a primarily aqueous solution, or concentrating to remove the methanol and optionally thereafter adding water;

(3) adding a water-immiscible organic solvent, such as a water-immiscible oxygenated organic solvent or an aromatic or halogenated hydrocarbon solvent, to the aqueous solution or residue and intimately contacting to extract or partition the active component into the water-immiscible solvent layer and then separating and concentrating the non-aqueous solution;

(4) subjecting the material recovered in Step (3) to adsorption chromatography or to a combination of absorption and partition chromatography wherein in each chromatographic separation, the active component from the eluates exhibiting activity against Candida albicans are combined and concentrated to recover Compound IA.

The exact steps may vary somewhat depending on whether the fermentation had been carried out in liquid or solid medium, what solvent is employed and what adsorbent or combination of adsorbents is employed.

When the fermentation is carried out in solid medium, the first step may be carried out by adding an alcoholic solvent to the fermentation medium, thoroughly mixing, then filtering, recovering and concentrating the aqueous alcohol filtrate. The filtrate is extracted or partitioned with a water-immiscible oxygenated organic solvent or an aromatic or halogenated hydrocarbon solvent and the resulting water-immiscible solvent solution concentrated, loaded onto a column for at least one, generally several separation steps by adsorption chromatography which may be combined with partition chromatography.

When the fermentation is carried out in a liquid medium, the mycelial solids are filtered and recovered from the fermentation medium. Alcohol is added to the mycelial cake, and the mycelial solid thoroughly mixed with the alcohol, filtered, and the filtrate collected and concentrated. Then in a manner similar to that described for isolation from solid media, the alcoholic aqueous solution is intimately admixed with a water-immiscible oxygenated organic solvent or an aromatic or halogenated hydrocarbon solvent to extract or partition the product thereinto, and the resulting solution then employed in chromatographic separations.

The alcoholic solvent to be employed in the initial extraction of the active agent from the solid nutrient medium or from the mycelial pad may be any of the lower alcohols such as methanol, ethanol, isopropanol, and the like. Methanol is preferred.

The water-immiscible non-polar organic solvent useful for extracting or partitioning the active agent from the methanol solution are esters, such as ethyl acetate, isopropyl acetate, butyl acetate and the like and ketones, such as methyl ethyl ketone. However, halohydrocarbons such as methylene chloride and aromatic hydrocarbons such as benzene or toluene may be employed. Lower aliphatic esters are preferred.

The chromatographic separation may be carried out by employing conventional column chromatography with non-ionic resin. The fractions containing the antibiotic Compound IA may be detected by bioautography using Candida albicans. As in isolation from solid fermentation media, generally more than one chromatographic separation steps are employed.

Silica gel is the preferred adsorbent but may be alternated with other adsorbents. Various grades of silica gel and sizes of silica gel are available commercially (from E. Merck or as Kieselgel from E.M. Science). Other adsorbents such as alumina, styrene-divinylbenzene copolymers available commercially as Diaion HP-20, HP-30, HP-40 (Mitsubishi Chemical Industries, Ltd.) and Amberlite XAD-2, XAD-4, XAD-16 (Rohm and Haas Co.) also may be employed.

Partition chromatography may be used in combination with adsorption chromatography. The agent used for partition chromatography is a chemically modified dextran commercially available in several grades as Sephadex from Pharmacia.

The extracted or partitioned material from the fermentation containing the desired product may be fractionated in isocratic, step gradient or continuous gradient systems. When silica gel is the adsorbent, ester and exter/alkane mixtures especially, ethyl acetate/hexane mixtures have been useful eluting solvent. When a dextran is employed, a chlorohydrocarbon/hydrocarbon/alcohol solvent system is useful. A mixture of methylene chloride/hexane/methanol has been found to be especially useful.

In a preferred procedure, the separation is carried using several grades of silica gel for adsorption chromatography and Sephadex for partition chromatography.

The product rich fraction from each chromatographic separation may be identified with *Candida albicans* assay and these fractions then may be combined and concentrated for further purification or for recovery. The final purification is preferably partition chromatography employing Sephadex LH-20 and methylene chloride/hexane/methanol (10:10:1) at a slow flow rate of about 2 milliliters per minute. The eluate may then be concentrated to recover the antibiotic product.

The compounds of the present invention in which R is a lower alkanoyl group may be prepared by reacting Compound IA with an acylating agent in the presence of a base. The preferred acylating agents are acid anhydrides and acid halides. When the acyl group is acetyl, either acetyl halide or acetic anhydride may be employed. When the acyl group is higher, acyl halide is preferably employed.

The reaction may be carried out in a basic organic solvent such as pyridine or picoline but also may be carried out in an aromatic hydrocarbon containing a tertiary amine base. With acetic anhydride, excess acetic anhydride may be used as solvent with sufficient tertiary amine base to be a hydrogen acceptor.

In a preferred procedure, Compound IA is dissolved in pyridine and the acid anhydride or acid halide is added, dropwise at room temperature or with cooling to obtain the desired product. The product may be recovered according to conventional procedures.

The broad antifungal activity of the compounds of the present invention may be illustrated with representative assay results showing activity of Compound IA against a variety of filamentous fungi and yeasts in a disk diffusion assay. The organisms used in such assays were stock cultures of filamentous fungi maintained on potato dextrose agar (Difco) and transferred serially at two week interval using standard microbiological techniques or strains of yeasts maintained frozen at $-80°$ C. in 20 percent aqueous glycerol.

Seeded agar assay plates were prepared according to the type of assay strain. Inoculum for filamentous fungi was prepared by scraping the surface of stock plates with a moistened sterile dacron swab. The spores and mycelium were then suspended in 10 milliliters of sterile potato dextrose broth (PDB) and adjusted to 70% transmittance (T) at 660nm. Inoculum for yeasts was prepared from overnight broth cultures. Cultures were then diluted into PDB to a final concentration of either 40% or 70% T at 660nm. Assay plates were prepared by diluting the inoculum into appropriate molten agar medium, cooled to 45° C., to yield a final concentration of 4%.

Samples were applied to 6.2 mm filter paper disks (25 ml/disk) and air dried at 24° C. The disks were then applied to seed assay plates with sterile forceps, and rewetted with 25% sterile aqueous dimethyl sulfoxide (DMSO). The assay plates were then incubated at either 28° or 37° C. for 24 hours.

Following incubation, inhibition zones were measured and recorded. Measurement was made from the extreme edge of any zone where the growth differs from the background lawn. Inhibition zones were further qualified as follows: fuzzy (F)—a zone that had a fuzzy edge and clear center surrounding the disc, hazy (H)—a zone that was hazy throughout, slightly hazy (S)—a zone in which low levels of growth were discernible throughout the inhibition zone, and very hazy (V) - a zone in which the differences between the background lawn and inhibition zone where barely discernable. Zones without a qualifier were clear throughout. Representative results are seen in the following table.

| Culture Number | Media[a] | Temp °C. | Microbial Species | Concentration Compound IA | | |
|---|---|---|---|---|---|---|
| | | | | 1000 μg/ml | 500 μg/ml | 250 μg/ml |
| MY34 | YED | 28 | *Saccharomyces cerevisiae* | 20S | 17S | 15S |
| MY992 | YED | 28 | *Candida albicans* | 12H | 10H | 9V |
| MF4626 | PDA | 28 | *Cochliobolus miyabeanus* | 40F | 36S | 32S |
| MF442 | YED | 28 | *Aspergillus niger* | 13S | 10H | 8V |
| MF11 | PDA | 28 | *Aspergillus niger* | 12S | 10S | 8H |
| MF3560 | PDA | 28 | *Trichoderma lignorum* | 19H | 16H | 13V |
| MF1996 | PDA | 28 | *Ustilago zeae* | 27S | 24S | 20S |
| MF4042 | PDA | 28 | *Ceratocystis ulmi* | 23F | 20S | 17H |
| MF3550 | PDA | 28 | *Alternaria solani* | 32F | 30F | 29S |
| MF3794 | PDA | 28 | *Verticillium serrae* | 21F | 17S | 13H |
| MF4641 | PDA | 28 | *Cephalosporium sp.* | 9H | 8V | 0 |
| MF4608 | PDA | 28 | *Cercospora beticola* | 20H | 18H | 15H |
| MY1012 | SDA | 37 | *Candida tropicalis* | 25F | 21F | 18F |
| MY1028 | SDA | 37 | *Candida albicans* | 10H | 8V | 0 |
| MY321 | SDA | 28 | *Torulospora hansenii* | 14S | 12S | 9H |
| MY410 | PDA | 28 | *Saccharomyces cerevisiae* | 11S | 8S | 0 |
| MY1074 | SDA | 28 | *Cryptococcus laurentii* | 22S | 17S | 15S |
| MY1100 | SDA | 37 | *Candida pseudotropicalis* | 16S | 13S | 8S |
| MY1070 | SDA | 28 | *Cryptococcus albidus* | 12H | 9V | 0 |
| MY1073 | SDA | 28 | *Cryptococcus laurentii* | 19H | 15H | 13H |
| MY1077 | SDA | 28 | *Cryptococcus laurentii* | 17H | 15H | 12H |
| MY1113 | SDA | 28 | *Kluyveromyces fragilis* | 14S | 10S | 8H |
| MY1055 | SDA | 28 | *Candida albicans* | 9V | 8V | 0 |
| MF4784 | PDA | 37 | *Rhizonmucor miehei* | 9H | 7V | 0 |
| MF383 | PDA | 28 | *Aspergillus flavus* | 15S | 12S | 9H |

-continued

| Culture Number | Media[a] | Temp °C. | Microbial Species | Concentration Compound IA | | |
|---|---|---|---|---|---|---|
| | | | | 1000 μg/ml | 500 μg/ml | 250 μg/ml |
| MF4839 | PDA | 28 | *Aspergillus fumigatus* | 14S | 8H | 0 |

[a]Difco PDA = Potato Dextrose Agar;
SDA = Sabouraud Dextrose Agar;
YED = Yeast Extract Dextrose The compound is especially effective against organisms such as *Cochliobolus miyabenus* and *Alternaria solani* with which at concentration as low as 16 ug/ml zones of inhibition measuring 17S and 13H respectively are observed.

The antifungal properties of the present invention may be effectively utilized by administering an antifungal amount of a compound of Formula I to or in the area, object or subject on or in which control of fungi is desired. The amount of the compound of Formula I to be employed depends on the compound and particular fungal organism to be controlled and the particular environment in which it is to be administered.

The antifungal properties are most effectively utilized when a compound of Formula I is formulated into antifungal treating composition with a biologically inert carrier which in cases of use for pharmaceutical application should also be pharmaceutically acceptable.

The compositions are formulated according to conventional compounding techniques with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in or on inanimate objects.

The novel compositions preferably contain 5 percent or more by weight of the active compound and, if a concentrate composition may contain 15 percent or more. In preparing the compositions, a compound of Formula I is intimately admixed with an appropriate conventional carrier.

For non-therapeutic applications, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

For therapeutic applications, the product of the present invention may be employed in compositions employing a carrier suitable for therapeutic application. Such carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, kaolin, talc, lactose, lubricants such as calcium stearate, binders, disintegrating agents and the like.

The compounds may be used in topical application. For such applications, the drug may be formulated in conventional creams and ointments such as white petrolatum, anhydrous lanolin, cetyl alcohol, cold cream, glyceryl monostearate, rose water and the like. Usually a 5 percent cream or solution is prepared and applied to the area to be treated.

The antifungal compositions may be utilized by applying to the areas where fungal control is desired.

The following examples illustrate the invention but are not to be construed as limiting.

EXAMPLE I

Solid Phase Flask Fermentation

The seed medium (Seed Medium I) was adjusted to pH 6,8 with NaOH, sterilized and a slant section of a preserved culture of *A. ochraceus* ATCC 22947 which had originally been obtained from American Type Culture Collection was inoculated into 50 milliliters of the sterilized medium, and the resulting medium cultured for 3 days on a rotary shaker (212 rpm, 2 inch throw) at 28° C. to obtain growth of *A. ochraceus* in the medium.

Two milliliters of the seed medium culture thereafter was transferred to a 250 milliliter unbaffled Erlenmeyer flask containing the following medium

| | |
|---|---|
| Cracked corn | 10.0 grams |
| Yeast hydrolysate (Ardamine, PH) | 2.0 mg |
| KH$_2$PO$_4$ | 1.0 mg |
| MgSO$_4$.7H$_2$O | 1.0 mg |
| Sodium tartrate | 1.0 mg |
| FeSO$_4$.7H$_2$O | 0.1 mg |
| ZnSO$_4$.H$_2$O | 0.1 mg |
| Distilled water | 25 ml |

After inoculation, the flasks were incubated for fourteen days on a rotary shaker (220 rpm, 2 inch throw) at 25° C. to obtain an antibiotic product in the fermentation medium.

EXAMPLE II

Liquid Phase Fermenter Fermentation

A slant of a lyophilized culture of *A. ochraceus*, ATCC 22947, was used to inoculate 50 milliliters of a seed medium of the same compositon as the seed medium in Example I. The seed flask was then incubated at 28° C. for 48 hours on a rotary shaker at 220 rpm. Two percent (1.0 milliliter) of the inoculum was used to inoculate 500 milliliters of the seed medium previously described contained in 2 liter unbaffled Erlenmeyer flasks and the seed flasks incubated at 28° C. for 24 hours on a rotary shaker at 200 rpm.

Production medium of the following composition in distilled water

| | |
|---|---|
| Dextrose | 10.0 g/l |
| Glycerol | 10.0 g/l |
| Corn steep liquor | 5.0 g/l |
| (NH$_4$)$_2$SO$_4$ | 2.0 g/l |
| Corn meal | 10.0 g/l |
| CoCl$_2$.6H$_2$O | 10.0 mg/l |
| Soybean meal | 5.0 g/l |
| Glycine | 2.0 g/l |

11
-continued

| P-2000 antifoam (Dow) | 3.0 ml/l | was adjusted to pH 7.0, sterilized, and then inoculated with 5 percent inoculum (2.5 milliliters) in four 14-liter fermentors, each containing 10 liters of production medium. The fermentations were carried out at 28° C. under an airflow range of 2.0 to 5.0 liters/minute and agitation rate of 200 to 500 rpm for 90 hours to obtain an antibiotic product in the fermentation medium.

EXAMPLE III

Isolation of Compound IA from Solid Phase Fermentation Medium

Fermentation products contained in solid fermentation media in thirty-four 250-milliliter flasks (each flask initially containing 35 grams of a corn based fermentation medium of the composition ratio of Example I) were recovered by first adding 100 milliliters of methanol to each flask with stirring to break up the solid medium and steeping overnight at room temperature and then filtering to obtain 2600 milliliters of filtrate. The spent mycelium was extracted again with methanol and filtered to obtain 2500 milliliters of filtrate.

The filtrate from the first extraction (2600 ml) was partitioned into two layers by adding 650 milliliters of water and 3250 milliliters of methylene chloride to make a mixture of the following ratio 4:1:5 methanol extract/water/methylene chloride. The methylene chloride/methanol layer was separated from the methanol/water layer. The methylene chloride/methanol layer was found to contain all the antifungal activity as determined by zone of growth inhibition of C. albicans MY 992 in an agar disk diffusion assay.

A similar operation was carried out on the second methanol extract (2500 ml filtrate) and the methylene chloride/methanol layers from the two operations were combined and concentrated to dryness to obtain a residue which was dissolved in 100 milliliters of ethyl acetate and chromatographed on 1 liter of silica gel (E. Merck Grade 62, 60–200 mesh) using ethyl acetate as the eluting agent. The antibiotic product rich fractions (as determined by C. albican bioautography) were rechromatographed on 200 milliliters of silica gel (EM Science, Kieselgel 60 230–400 Mesh) using ethyl acetate as eluting agent.

The product rich fractions from the second silica gel chromatography were combined and concentrated to dryness. The resulting residue was dissolved in 2 milliliters of a solvent mixture of hexane/methylene chloride/methanol (10:10:1) and chromatographed on 100 milliliters of Sephadex LH-20 in the same solvent system. The product rich fractions from this chromatography were combined and concentrated to obtain 18.9 milligrams of a product which was characterized to be Compound IA and having the physical properties previously set forth.

12

EXAMPLE IV

2-Benzyl-1-methyl-5-(n-nonyl)pyrrolidin-3-yl acetate

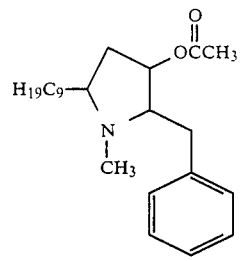

16.6 milligrams ($5 \times 10^{-5}$ mole) of 2-benzyl-1-methyl-5-(n-nonyl)pyrrolidin-3-ol was dissolved in pyridine and 10 drops (0.54 g) of acetic anhydride was added at room temperature whereupon a reaction took place with the formation of 2-benzyl-1-methyl-5-(n-nonyl)pyrrolidin-3-yl acetate. The product was recovered from the reaction mixture is a conventional manner by vaporizing off the solvent. The product after drying had the NMR properties previously detailed.

EXAMPLE V

In similar operations but using propionyl chloride or t-butyryl chloride in pyridine, the following compounds may be prepared:

(1) 2-benzyl-1-methyl-5-nonyl-pyrrolidin-3-yl propionate.
(2) 2-benzyl-1-methyl-5-nonyl-pyrrolidin-3-yl t-butyrate.

EXAMPLE VI

An ointment suitable for topical antifungal application may be prepared by intimately dispersing 5 grams of 2-benzyl-1-methyl-5-(n-nonyl)-pyrrolidin-3-ol in 100 grams of commercially available polyethylene/hydrocarbon gel.

An ointment also may be prepared from 6 grams of 2-benzyl-1-methyl-5-(n-nonyl)pyrrolidin-3-yl acetate and 100 grams of polyethylene hydrocarbon gel.

EXAMPLE VII

Powder formulations for non-pharmaceutical antifungal application may be prepared by intimately admixing 50 parts by weight of 2-benzyl-1-methyl-5-(n-nonyl)pyrrolidin-3-ol with 50 parts by weight of predispersed coating clay.

EXAMPLE VIII

The following liquid compositions may be prepared for antifungal use:

| | |
|---|---|
| (1) 2-Benzyl-1-methyl-5-(n-nonyl)pyrrolidin-3-ol | 25 parts by weight |
| Xanthan gum | 0.6 part by weight |
| Water | 74.4 part by weight |
| (2) 2-Benzyl-1-methyl-5-(n-nonyl)pyrrolidin-3-yl acetate | 20 parts by weight |
| Polyethylene glycol 200 | 80 parts by weight |

What is claimed is:
1. A compound represented by the formula

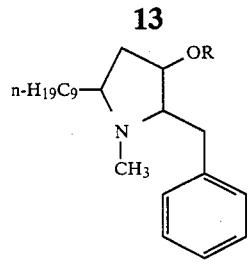
wherein R is hydrogen or lower alkanoyl.
2. A compound according to claim 1 wherein R is hydrogen.
3. A compound according to claim 1 wherein R is acetyl.
4. An antifungal composition which comprises a compound of claim 1 in admixture with a biologically inert carrier.
5. A composition according to claim 4 in which the carrier is a pharmaceutically acceptable carrier.
* * * * *